(12) United States Patent
Ercan et al.

(10) Patent No.: US 9,221,037 B2
(45) Date of Patent: Dec. 29, 2015

(54) MULTIMETAL ZEOLITES BASED CATALYST FOR TRANSALKYLATION OF HEAVY REFORMATE TO PRODUCE XYLENES AND PETROCHEMICAL FEEDSTOCKS

(71) Applicants: Saudi Arabian Oil Company, Dhahran (SA); King Fahd University of Petroleum and Minerals, Dhahran (SA)

(72) Inventors: Cemal Ercan, Dhahran (SA); Yuguo Wang, Dhahran (SA); Mohammed Ashraf Ali, Dhahran (SA); Sulaiman Saleh Al-Khattaf, Dhahran (SA); Syed Ahmed Ali, Dhahran (SA); Abdullah Mohammed Aitani, Al-Khobar (SA)

(73) Assignees: SAUDI ARABIAN OIL COMPANY (SA); KING FAHD UNIVERSITY OF PETROLEUM AND MINERALS (SA)

( * ) Notice: Subject to any disclaimer, the term of this patent is extended or adjusted under 35 U.S.C. 154(b) by 157 days.

(21) Appl. No.: 13/796,383

(22) Filed: Mar. 12, 2013

(65) Prior Publication Data
US 2013/0261364 A1 Oct. 3, 2013

Related U.S. Application Data

(60) Provisional application No. 61/619,161, filed on Apr. 2, 2012.

(51) Int. Cl.
*B01J 29/80* (2006.01)
*C07C 6/12* (2006.01)
(Continued)

(52) U.S. Cl.
CPC ............... *B01J 29/80* (2013.01); *B01J 29/005* (2013.01); *B01J 29/061* (2013.01); *B01J 29/068* (2013.01);
(Continued)

(58) Field of Classification Search
CPC  C07C 6/123; C07C 2529/40; C07C 2529/80; C07C 2529/85; C07C 6/126; C07C 2529/70; B01J 29/80; B01J 29/405; B01J 37/04; B01J 2229/18; B01J 29/7007; B01J 29/44; B01J 29/7615; B01J 29/78; B01J 29/85; B01J 29/84; B01J 29/7815; B01J 2229/186; B01J 29/7049; B01J 29/76; B01J 29/741; B01J 29/068; B01J 29/74; B01J 2229/20; B01J 2029/062; B01J 29/42; B01J 29/40; B01J 37/0201; B01J 2229/42; B01J 29/061; B01J 29/7215; B01J 29/005; B01J 29/46; B01J 29/48; B01J 29/7057; B01J 29/076; B01J 29/72; B01J 29/222; B01J 29/7415; C10G 45/64
USPC .......................... 502/65, 66, 67, 71; 585/475
See application file for complete search history.

(56) References Cited

U.S. PATENT DOCUMENTS 3,679,769 A    7/1972  Kmecak et al.
3,699,181 A  * 10/1972  Kmecak et al. ............... 585/321
(Continued)

FOREIGN PATENT DOCUMENTS

CN   101172924 A   5/2008
CN   101190866 A   6/2008

OTHER PUBLICATIONS

PCT International Search Report and The Written Opinion dated Aug. 19, 2013; International Application No. PCT/US2013/030579; International File Date: Mar. 12, 2013.

*Primary Examiner* — In Suk Bullock
*Assistant Examiner* — Aaron Pierpont
(74) *Attorney, Agent, or Firm* — Bracewell & Giuliani LLP; Constance Gall Rhebergen

(57) ABSTRACT

A transalkylation catalyst for the transalkylation of a heavy reformate is provided. The catalyst includes two solid acid zeolites having different physical and chemical properties, and at least three metals selected from the group 4 lanthanthides, and the elements found in groups 6 and 10 of the periodic table.

8 Claims, 3 Drawing Sheets

(51) Int. Cl.
| | |
|---|---|
| B01J 37/04 | (2006.01) |
| B01J 29/00 | (2006.01) |
| B01J 29/06 | (2006.01) |
| B01J 29/068 | (2006.01) |
| B01J 29/072 | (2006.01) |
| B01J 29/076 | (2006.01) |
| B01J 29/40 | (2006.01) |
| B01J 29/42 | (2006.01) |
| B01J 29/44 | (2006.01) |
| B01J 29/46 | (2006.01) |
| B01J 29/48 | (2006.01) |
| B01J 29/70 | (2006.01) |
| B01J 29/72 | (2006.01) |
| B01J 29/74 | (2006.01) |
| B01J 29/76 | (2006.01) |
| B01J 29/78 | (2006.01) |
| B01J 29/84 | (2006.01) |
| B01J 29/85 | (2006.01) |
| B01J 37/02 | (2006.01) |
| C10G 45/64 | (2006.01) |
| C10G 29/20 | (2006.01) |

(52) U.S. Cl.
CPC .............. *B01J 29/072* (2013.01); *B01J 29/076* (2013.01); *B01J 29/40* (2013.01); *B01J 29/405* (2013.01); *B01J 29/42* (2013.01); *B01J 29/44* (2013.01); *B01J 29/46* (2013.01); *B01J 29/48* (2013.01); *B01J 29/7007* (2013.01); *B01J 29/7049* (2013.01); *B01J 29/7057* (2013.01); *B01J 29/72* (2013.01); *B01J 29/7215* (2013.01); *B01J 29/74* (2013.01); *B01J 29/7415* (2013.01); *B01J 29/76* (2013.01); *B01J 29/7615* (2013.01); *B01J 29/78* (2013.01); *B01J 29/7815* (2013.01); *B01J 29/84* (2013.01); *B01J 29/85* (2013.01); *B01J 37/0201* (2013.01); *B01J 37/04* (2013.01); *C07C 6/123* (2013.01); *C07C 6/126* (2013.01); *C10G 29/205* (2013.01); *C10G 45/64* (2013.01); *B01J 2029/062* (2013.01); *B01J 2229/18* (2013.01); *B01J 2229/183* (2013.01); *B01J 2229/186* (2013.01); *B01J 2229/20* (2013.01); *B01J 2229/42* (2013.01); *C07C 2529/40* (2013.01); *C07C 2529/70* (2013.01); *C07C 2529/80* (2013.01); *C07C 2529/85* (2013.01)

(56) References Cited

U.S. PATENT DOCUMENTS

| | | | |
|---|---|---|---|
| 5,522,984 | A * | 6/1996 | Gajda et al. ............... 208/120.01 |
| 5,600,050 | A * | 2/1997 | Huang ....................... C07C 2/66 585/462 |
| 6,111,157 | A | 8/2000 | Hendriksen et al. |
| 6,858,129 | B2 | 2/2005 | Mohr et al. |
| 7,393,989 | B2 | 7/2008 | Negiz et al. |
| 7,419,931 | B2 | 9/2008 | Serra et al. |
| 7,553,791 | B2 | 6/2009 | McMinn et al. |
| 7,576,249 | B2 | 8/2009 | Xiao et al. |
| 7,605,295 | B1 | 10/2009 | Lafyatis et al. |
| 7,626,064 | B1 | 12/2009 | Boldingh et al. |
| 7,629,499 | B2 | 12/2009 | Serra Alfaro et al. |
| 7,687,423 | B2 | 3/2010 | Moscoso et al. |
| 7,897,825 | B2 | 3/2011 | Levin |
| 7,923,399 | B2 | 4/2011 | Long et al. |
| 8,022,261 | B2 | 9/2011 | Kalyanaraman et al. |
| 8,044,253 | B2 | 10/2011 | Negiz et al. |
| 8,071,828 | B2 | 12/2011 | Cao et al. |
| 8,163,966 | B2 | 4/2012 | Levin |
| 8,183,424 | B2 | 5/2012 | Levin et al. |
| 2006/0211902 | A1 | 9/2006 | Xiao et al. |
| 2008/0128324 | A1* | 6/2008 | Hansen ................ B01J 29/166 208/59 |
| 2010/0029467 | A1* | 2/2010 | Inui et al. ........................ 502/66 |
| 2010/0228066 | A1* | 9/2010 | Kong ..................... C10G 67/06 585/321 |

* cited by examiner

MULTIMETAL ZEOLITES BASED CATALYST FOR TRANSALKYLATION OF HEAVY REFORMATE TO PRODUCE XYLENES AND PETROCHEMICAL FEEDSTOCKS

CROSS REFERENCE TO RELATED APPLICATION

This application claims priority to and the benefit of U.S. Provisional Application Ser. No. 61/619,161, filed Apr. 2, 2012, the full disclosure of which is hereby incorporated by reference herein for all purposes.

FIELD OF THE INVENTION

This invention relates to a transalkylation catalyst. More specifically, this invention relates to the a transalkylation catalyst for the conversion of heavy reformate to a xylenes-rich product stream.

BACKGROUND OF THE INVENTION

Heavy reformate, which typically includes greater than about 90% by weight C9+ aromatics, has historically been blended into gasoline streams. With current regulations on the aromatics content and high end boiling point of gasoline, however, it is no longer possible to blend heavy reformate into gasoline. Considering the market growth rate of demand on para-xylene, the conversion of heavy aromatics to para-xylene by transalkylation is considered to be one economically viable way to utilize the heavy reformate.

The restrictions on the aromatics content in gasoline are compelling the petroleum refiners to find alternative routes for utilization of excess heavy reformate obtained from catalytic reforming of naphtha. Heavy reformate streams typically include a high concentration of C9+ aromatics, usually consisting of at least 90% by weight C9 aromatics. Thus, because of the strict restrictions on the content of aromatics in gasoline, additional uses for aromatics, such as are found in a heavy reformate stream, must be found.

SUMMARY OF THE INVENTION

Generally, a method for the transalkylation of a heavy reformate to produce a xylenes-rich stream is provided.

In one aspect, a method for the transalkylation of a heavy reformate is provided. The method includes providing a heavy reformate containing at least about 90% by weight C9+ aromatics and hydrogen gas to a transalkylation reactor. The transalkylation reactor is charged with a transalkylation catalyst to selectively convert the C9+ aromatics to a xylene-rich product stream. The transalkylation catalyst includes at least two solid-acid zeolites selected from the group consisting of mordenite, beta zeolite, ZSM-5, ZSM-11, ZSM-12, ZSM-22, ZSM-23, MFI topology zeolite, NES topology zeolite, EU-1, MAPO-36, SAPO-5, SAPO-11, SAPO-34, and SAPO-41, and at least three metal selected from the Group 4 lanthanides, Group 6, and Group 10 of the Periodic Table of the Elements. The product stream is then separated into a light gas recycle stream a C9+ heavy aromatic recycle stream and a mixed aromatics product stream. The mixed aromatics product stream is then separated into a benzene stream, a toluene stream and a xylenes stream. The light alkanes are then separated from the light gas recycle stream. The light alkanes are then supplied to a steam cracker, wherein the light alkanes are converted to mixed olefins.

In certain embodiments, the method also includes separating hydrogen gas from the light gas recycle stream and recycling the hydrogen gas to the transalkylation reactor. In certain embodiments, the transalkylation reaction zone is maintained at a temperature of between about 200 and 540° C. In certain embodiments, the transalkylation reaction zone is maintained at a pressure of between about 1 and 5 MPa. In certain embodiments, the ratio of hydrogen to heavy reformate is between about 0.1:1 and 10:1. In certain embodiments, the steam cracker includes a reaction zone that is maintained at a temperature of between about 600 and 850° C. In certain embodiments, the residence time of the light alkanes in the steam cracker reaction zone is less than about 0.1 seconds. In certain embodiments, the two solid acid zeolite components of the catalyst have different physical and chemical characteristics. In certain embodiments, the transalkylation catalyst includes a first solid acid zeolite that is present in an amount of between about 10 and 90% by weight of the total catalyst weight. In certain embodiments, the transalkylation catalyst includes a second solid acid zeolite that is present in an amount of between about 10 and 90% by weight of the total catalyst weight. In certain embodiments, the transalkylation catalyst further includes a binder selected from inorganic oxides. In certain embodiments, the metal components are present in an amount of between about 0.01 and 5% by weight of the total catalyst weight.

DETAILED DESCRIPTION OF THE INVENTION

Although the following detailed description contains many specific details for purposes of illustration, it is understood that one of ordinary skill in the art will appreciate that many examples, variations and alterations to the following details are within the scope and spirit of the invention. Accordingly, the exemplary embodiments of the invention described herein and provided in the appended figures are set forth without any loss of generality, and without imposing limitations, on the claimed invention.

As noted above, heavy reformate streams typically have high concentrations of C9+ aromatics. Due to strict restrictions on the amount of aromatics that can be included in gasoline, portions of these streams cannot be used directly as gasoline additives. One economically viable option for making use of the aromatics found in heavy reformate streams is to convert the C9+ aromatics present in the stream into xylenes by transalkylation.

Transalkylation allows for the integration of certain refining processes and results in the production of economically valuable petrochemicals. The extra C9+ aromatics that result from the refining process that are typically rejected and removed from the gasoline blending pool, for example, because of environmental regulations and maximum boiling point restriction, can then be used as a feedstock for production of valuable petrochemicals such as para-xylene, as well as certain light olefins, such as ethylene, propylene, and butenes.

Steam cracking is one petrochemical process by which saturated hydrocarbons can be broken down into smaller, often unsaturated, hydrocarbons. It is the most common industrial method for producing light alkenes (i.e., olefins), including ethene and propene.

Feedstocks provided to the transalkylation process can include heavy reformate. The composition of an exemplary heavy reformate is provided in Table 1.

TABLE 1

Exemplary Heavy Reformate Composition.

| Major Compound | Composition (wt. %) |
| --- | --- |
| Iso-propyl benzene | 1.7 |
| n-propyl benzene | 4.3 |
| 1-methyl-2-ethyl benzene | 6.5 |
| 1-methyl-3-ethyl benzene | 18.5 |
| 1-methyl-4-ethyl benzene | 9.1 |
| 1,2,3-tri-methyl benzene | 6.6 |
| 1,2,4-tri-methyl benzene | 39.0 |
| 1,3,5-tri-methyl benzene | 10.0 |
| Total C9 aromatics | 95.9 |
| n-butyl benzene | 0.5 |
| 1,4-diethyl benzene | 0.8 |
| 1,3-diethyl benzene | 0.4 |
| 1,3-dimethyl,5-ethyl benzene | 0.8 |
| 1,4-dimethyl,2-ethyl benzene | 0.4 |
| Other C10 compounds | 1.2 |
| Total C10 aromatics | 4.1 |

Figure 1:
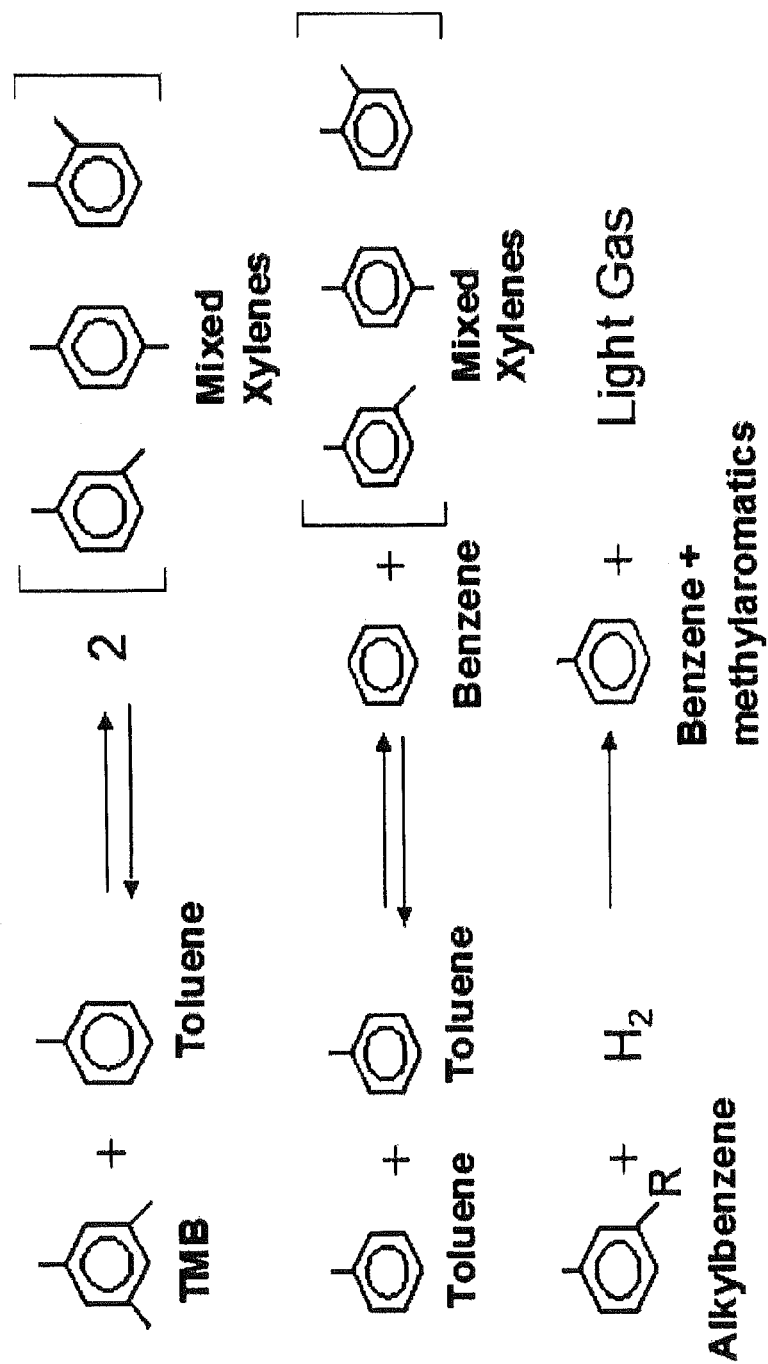
FIG. 1 shows desired transalkylation reactions.
Figure 2:
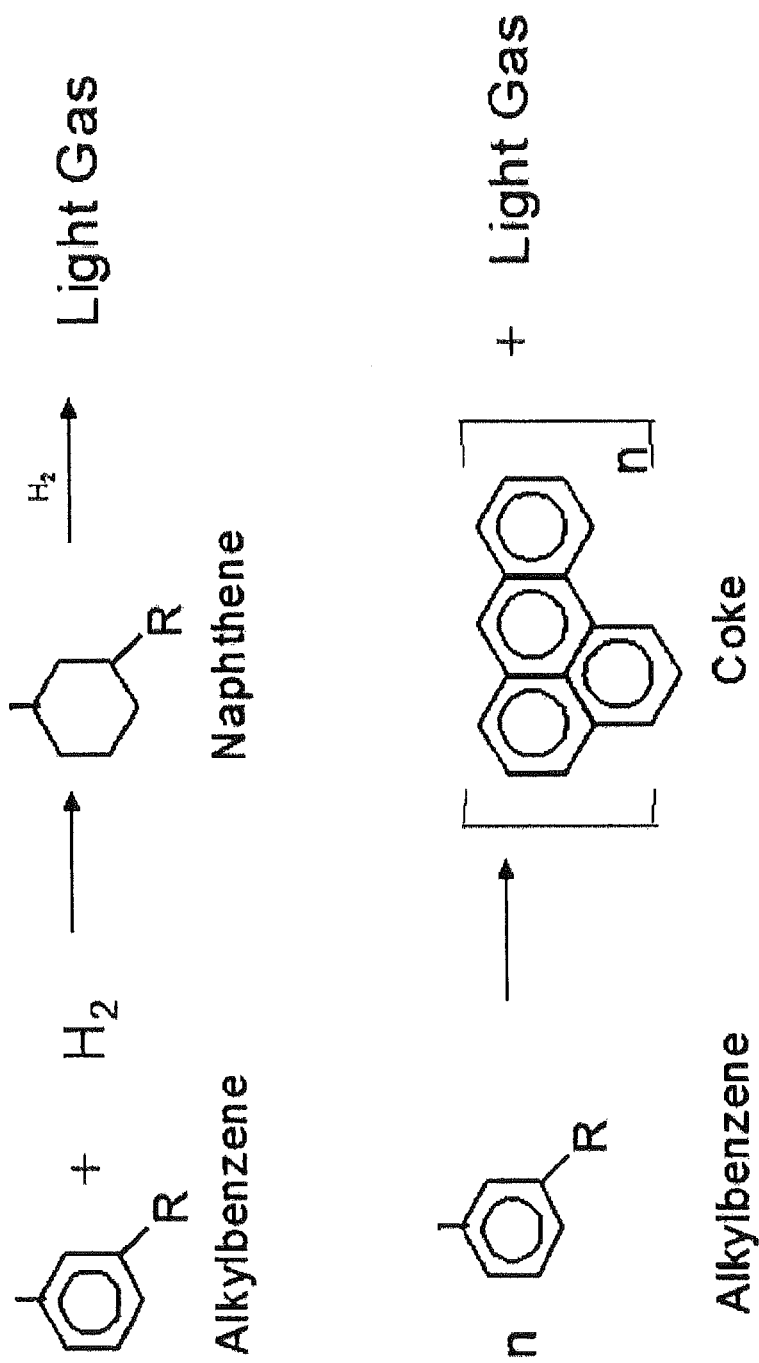
FIG. 2 shows undesired transalkylation side reactions.

In certain embodiments, an integrated process is provided wherein a heavy reformate feedstock can be utilized as the hydrocarbon feed to a transalkylation process to produce xylenes and by-product light gases. The light gases can include light paraffins that can then be fed into a steam cracker for the production of light olefins. During the transalkylation of the heavy reformate feedstock, as shown in FIG. 1, the most desirable reactions lead to the production of mixed xylenes, benzene, and methyl aromatics. Undesirable side reactions are shown in FIG. 2. During the transalkylation reaction, approximately 10-20% by weight of the light gases that are present, which generally include C1-C5 paraffins, are produced. A typical composition of the light gases produced by the transalkylation of a heavy reformate is listed in Table 2.

TABLE 2

Composition of light gases produced in the catalytic transalkylation of heavy reformate at reaction temperature of 400° C.

| Compound | Concentration (wt %) | Normalized concentration (wt %) |
| --- | --- | --- |
| Methane | 0.2206 | 1.44 |
| Ethane | 10.4601 | 68.41 |
| Propane | 3.7252 | 24.36 |
| Isobutane | 0.5212 | 3.41 |
| n-butane | 0.308 | 2.01 |
| Isopentane | 0.0558 | 0.37 |

In certain embodiments, provided is a method for using heavy reformate for the production of xylenes through transalkylation, and the subsequent use of by-product light gases as the feedstock to a steam cracker for the production light olefins, such as ethylene, propylene and butadiene. In this regard, in certain other embodiments provided is an integrated apparatus for transalkylation processes and steam cracking processes. Paraffin gases resulting from the transalkylation process can then be used as a feedstock for the steam cracker.

Figure 3:
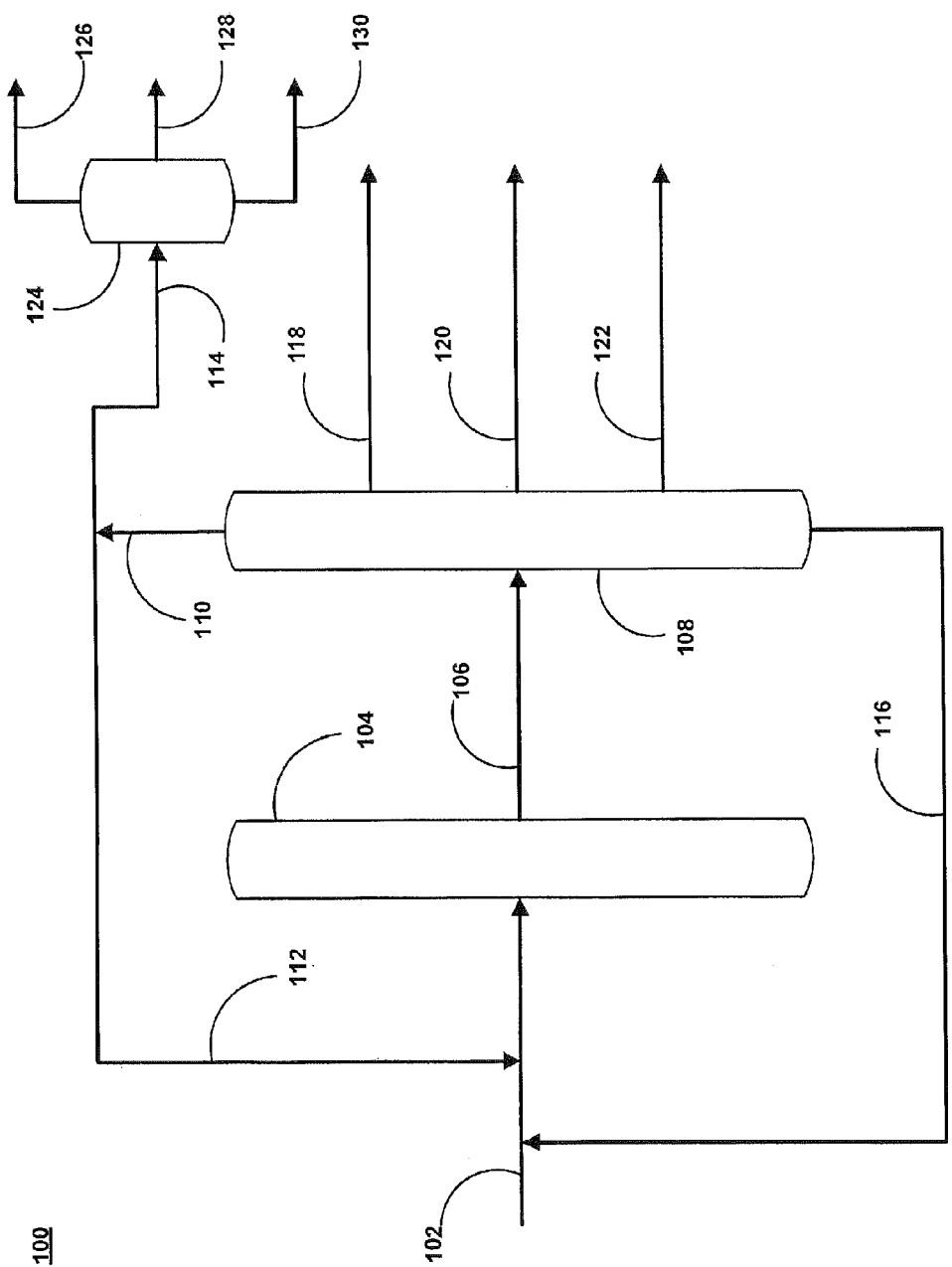
FIG. 3 is a schematic of a transalkylation apparatus according to one embodiment described herein.

A schematic of one embodiment of an integrated process for the transalkylation of heavy reformate and the subsequent steam cracking of light gases is provided in FIG. 3. A heavy reformate feed and hydrogen gas is provided via line 102 to transalkylation reactor 104. Transalkylation reactor 104 can include the transalkylation catalyst described herein in a transalkylation reaction zone. The transalkylation effluent product stream from transalkylation reactor 104 can be supplied via line 106 to splitter 108, which separates the product stream into a light gas recycle stream 110, a C9+ heavy aromatic recycle stream 116, a mixed aromatics product stream, that can then be separated into a benzene stream 118, a toluene stream 120 and a xylene stream 122. Light gas recycle stream 110 can include hydrogen, as well as light alkanes, and can be supplied via line 114 to the reaction zone of ethane steam cracker 124, which produces light olefins, including ethylene, propylene and butadiene, which are collected via lines 126, 128 and 130, respectively. Alternatively, the light recycle stream can be diverted to other uses, such as to benzene and toluene recovery, or alternatively can be recycled partially to the transalkylation zone. Optionally a portion of the light olefin stream can be recycled with hydrogen from splitter 108 via line 112 to the transalkylation reactor 104. Similarly, C9+ heavy aromatic recycle stream 116 can be partially or wholly recycled to transalkylation reactor 104, where it can be combined with feedstock and hydrogen gas supplied via line 102. Alternatively, C9+ heavy aromatic recycle stream can be removed from the process for disposal or other processing.

As used herein, "mixed xylenes" refers a class of C8 aromatics used for the production of para- and ortho-xylene, and in certain applications as solvents. These compounds have many different uses and can be used as feedstock for the preparation of certain industrial scale chemical reactions.

For example, para-xylene can be used as a principal feedstock for the preparation of polyester, which continues to enjoy a high growth rate from large base demand; ortho-xylene can be used as feedstock for the preparation of phthalic anhydride, which is used in high-volume and has mature markets; and meta-xylene can be used for the preparation of various products, such as plasticizers, dyes and wood preservatives, although typically in lesser but growing volumes as compared with ortho- and para-xylene. Ethylbenzene is another compound that can be present in xylene mixtures, and is occasionally recovered for use in the production of styrene. Ethylbenzene, however, is generally considered to be a less desirable component of C8 aromatics, and for this reason is not always separated and recovered.

In general, the production of xylenes can be increased in a variety of known ways. For example, xylene production can be increased through: (i) xylenes isomerization, (ii) toluene dis-proportionation, and (iii) transalkylation of toluene and C9+ aromatics. Comparing the economics of the various different processes for increasing xylenes production depends upon a variety of factors, including the current market situation, separation costs, C9+ aromatics availability, and environmental concerns. Transalkylation of toluene is a maximum xylene production mode and disproportionation is a maximum benzene production mode. The flexibility of the reaction mode that is selected enables a transalkylation unit to be operated in accordance with market dynamics and feedstock availability.

The transalkyaltion of heavy aromatics into xylenes described herein is one method for complying with the current stringent gasoline specifications, thereby responding to a future decline in gasoline demand and complying with growing market demands of xylenes and benzene. Whereas heavy aromatics were previously used as additives, now the transalkylation of heavy aromatics allows for certain synergies between the refining and petrochemical operations to be realized. The economics of the transalkylation of heavy aromatics depends on the price differential between gasoline and xylene, and can, in certain instances, be further influenced by site specific constraints. Although higher in investment compared to classical xylenes production, transalkylation can be successful in an environment with low reformate availability.

Typical aromatic production processes yield xylene mixtures having a ratio approaching thermodynamic equilibrium (i.e., about 24:53:23 for para-, meta-, and ortho-xylene isomers, respectively), while the current market demand for each of these xylene isomers is in the ratio of about 80:2:18. Efforts have been made to adjust the composition of the xylene mixture beyond the thermodynamic value. These efforts have included certain innovations both in catalyst development and process design.

Typically, production of mixed xylenes can be achieved via catalytic naphtha reforming, particularly when used in recovery of and purification into ortho- or para-xylene. Alternatively, mixed xylenes can also be recovered from pyrolysis gasoline (an aromatic-rich by-product of an ethylene cracker process), but the ethylbenzene content of the resultant stream is generally prohibitively high, thereby limiting use in the solvent market.

In certain embodiments, it is desirable to increase the yield of xylenes and to de-emphasize benzene production. It is understood that demand for xylene derivatives is growing at a greater rate than demand for benzene derivatives. In certain processes, refinery modifications can be effected to reduce the benzene content of gasoline in industrialized countries, which will in turn increase the supply of benzene available to meet demand. A higher yield of xylenes at the expense of benzene, thus, is a favorable objective and the result of certain processes described herein. In certain embodiments, processes to transalkylate C9+ aromatics along with benzene or toluene have been commercialized, resulting in high xylene yields.

In certain embodiments, mixed xylenes can be obtained from the disproportionation of toluene or the transalkylation of C9 aromatics. The various production routes (and the considerations) can include: distillation of mixed xylenes (C8 aromatics feed at blend value); extraction of xylenes (with C8 aromatics at gasoline blending value, and extraction costs distributed on a prorated yield basis across benzene, toluene and xylenes (BTX)); conventional toluene disproportionation (with toluene at its extraction cost and market value as pertinent); selective toluene disproportionation producing benzene and xylenes in similar proportions, while permitting the selective production of para-xylene (with toluene at its extraction cost and market value as pertinent); combined toluene disproportionation and C9 transalkylation (with toluene at its chemical value and market value and the C9 aromatics at its gasoline blend value as pertinent); and transalkylation alone (which treats feeds comprising heavy reformate C9+ and produces principally xylenes and, in lower amounts, benzene and liquefied petroleum gases).

The complexity of xylene production can vary substantially depending upon the process employed. There can be, by design and unit synergy, much flexibility with which to vary the product slate regardless of the distribution of aromatics from the reforming unit. These processes can include processes to alkylate, dealkylate, isomerize, and disproportionate and/or transalkylate aromatics, such that the production of the desired aromatic can be increased from the distribution produced in the reforming unit. In certain embodiments, xylenes production can be selectively converted to any of the desired para-, meta- or ortho-xylene isomers by separating the desired component and reestablishing the equilibrium distribution of the remaining xylenes.

There are many known transalkylation processes for xylenes production available in the world chemical market. The primary function of all these processes is to increase the production of para-xylene from an aromatics complex by converting surplus low-value heavy aromatic streams to additional xylenes via rearrangement of the alkyl groups attached to the benzene ring. The selection of which process or technology to employ depends on many considerations, and generally the choice is the technology that offers the highest overall yield of para-xylene from fresh feedstock. Table 3 provides a list of the various advantages and disadvantages associated with certain major transalkylation processes, as well as the various properties of different transalkylation technologies.

TABLE 3

Properties of different transalkylation technologies.

| Technology | Advantages | Disadvantages |
|---|---|---|
| Toluene Disproportionation | No metals on catalyst, high quality benzene byproduct, and low hydrogen consumption | No utilization of heavy aromatics, low xylenes yield, high benzene yield, shorter catalyst cycle length |
| Selective Toluene Disproportionation | High para-xylene yield, no metals on catalyst, and low hydrogen consumption | No utilization of heavy aromatics, low xylenes yield, high benzene yield, shorter catalyst cycle length |
| Transalkylation of Toluene and $C_9$ Aromatics | Highest xylenes yield, low benzene yield, no metals on catalyst, high-quality benzene byproduct, low hydrogen consumption | Low utilization of $C_{10}$, $C_{11}$, shorter catalyst cycle length |
| Transalkylation of Toluene and $C_9/C_{10}$ | High xylenes yield, low benzene yield, longer catalyst cycle length, higher utilization of $C_{10}$, $C_{11}$ | Catalyst requires metals, benzene requires extraction |
| Transalkylation of $C_9/C_{10}$ | High xylenes yield, low benzene yield, longer catalyst cycle length, higher utilization of $C_{10}$, $C_{11}$ | No utilization of toluene, catalyst contains metals, benzene requires extraction, high hydrogen consumption |
| Transalkylation of Benzene and $C_9/C_{10}$ | Utilization of ethyl groups, utilization of surplus benzene, higher para-xylene yield | Shorter catalyst cycle length |

In certain embodiments, a solution is provided for the production of valuable xylenes from inexpensive heavy reformate feedstock. A typical composition of a heavy reformate feedstock contemplated for use herein is summarized in Table 1. The light gases, which are by products from transalkylation process and which include mainly light paraffins, can be further processed in a steam cracker to produce ethylene, propylene and butadiene. In certain embodiments, the catalyst utilized in the transalkylation process can be any of the catalysts described in U.S. Published Patent Application No. 2010/0029467. The transalkylation reaction temperature of the process can be in the range of between about 200-540° C., the reaction pressure can be between about 1-5 MPa, and liquid hourly space velocity can be between about 1-5 per hour. The ratio of hydrogen to heavy reformate ratio can be between about 1 to 4.

As shown in FIG. 3, liquid products from the transalkylation include benzene, toluene, and xylenes. Hydrogen gas and C9+ hydrocarbons can be separately recycled back into the transalkylation reactor. The light gas, such as may be collected from the top of the splitter, can be recovered and supplied into a steam cracker under typical steam cracker reaction conditions to produce ethylene, propylene and butadiene. As is known in the art, steam cracking is a process by which saturated hydrocarbons can be broken down into smaller, often unsaturated, hydrocarbons. Steam cracking is a principal industrial method for producing light alkenes (or olefins), including ethene (or ethylene) and propene (or propylene).

Generally, during steam cracking, a gaseous or liquid hydrocarbon feed like naphtha, LPG or ethane is diluted with steam and then heated in a furnace. The reaction temperature is typically very high, greater than about 600° C. and typically about 850° C., but the reaction residence time is very short, typically less than 0.1 seconds and more frequently less than about 0.01 seconds, resulting in gas velocities reaching speeds beyond the speed of sound, in an effort to improve the yield of desired products. After the cracking temperature has been reached, the gas is quickly quenched in a transfer line heat exchanger to stop the reaction.

The products produced by the steam cracking reaction will depend upon the specific composition of the feedstock, the hydrocarbon to steam ratio, and the cracking temperature and furnace residence time.

In certain embodiments, based upon the transalkylation reaction conditions, the light hydrocarbon feedstock (which can include ethane, LPGs, or light naphtha) can produce a product stream that is rich in the lighter alkenes, such as ethylene, propylene, and butadiene.

Tables 4 and 5 provide recent trends for gasoline specification trends in North America and Europe. As shown in each of the tables, the amount of aromatic content has steadily declined. This makes it necessary to find other uses for the heavy reformate produced catalytic reformers in refineries. The reduced RVP (Reid vapor pressure) also dictates for decreased reformate concentrations in gasolines.

TABLE 4

Trends in gasoline specification in North America

| Fuel (Gasoline) | Prior to 1994 | 1995-2000 | Beyond 2000 |
| --- | --- | --- | --- |
| Lead | Phase out | 0.0% | 0.0% |
| Benzene (vol %) | — | 1% | 0.8% |
| Aromatics (vol %) max | — | 25% | 22% |
| Olefin (vol %) max | — | — | 4% |
| Oxygen (vol %) min (oxygenates) | — | 2 | 2 |
| RVP psi | Lower RVP | 7.8/8.1 psi max | 7 psi max |

TABLE 5

Trends in gasoline specification in Europe

| Fuel (Gasoline) | 1994 | 1995 | 2000 | 2005 | 2010 |
| --- | --- | --- | --- | --- | --- |
| Sulfur (ppm max) | 1000 | 500 | 150 | 50/10 | <10 |
| Benzene (vol %) | 5% | — | 1% | 1% | <1% |
| Aromatics (vol %) max | — | — | 42% | 35% | <35% |
| Olefin (vol %) max | — | — | 18% | 18% | <10% |
| Oxygen (wt %) min (oxygenates) | — | 2.7% | 2.7% | 2.7% | — |

In preferred embodiments, the transalkylation reactor includes a novel multimetal zeolites-based catalyst developed for converting a heavy reformate feedstock into benzene, toluene, and xylenes (hereinafter, "BTX"), particularly commercially-valuable xylenes. Additionally, the multimetal zeolite-based catalyst produces petrochemical feedstocks, particularly C2 and C3 hydrocarbons, as a byproduct of the transalkylation reaction.

In certain embodiments, the multimetal catalyst can be formed by mixing at least two zeolites selected from the group consisting of mordenite, beta zeolite, ZSM-5, ZSM-11, ZSM-12, ZSM-22, ZSM-23, MFI topology zeolite, NES topology zeolite, EU-1, MAPO-36, SAPO-5, SAPO-11, SAPO-34, and SAPO-41, and the addition of at least three metal components selected from the Group 4 lanthanides and Group 10 of the Periodic Table of the Elements. The two zeolites should have different physical and chemical characteristics, such as pore size and acidity. One exemplary catalyst includes zeolites such as zeolite beta and ZSM-5, and metals such as cerium, nickel and platinum.

The transalkylation reaction can be conducted in one or more reactors with a fixed bed, moving bed, or radial flow reactor. The reaction temperature can be between about 200° C. and 540° C., alternatively between about 200° C. and 400° C., alternatively between about 350° C. and 540° C., alternatively between about 200° C. and 300° C., alternatively between about 300° C. and 400° C., alternatively between about 400° C. and 500° C., or alternatively between about 450° C. and 540° C. The reaction pressure can be between about 1 and 5 MPa, alternatively between about 1 and 3 MPa, alternatively between about 3 and 5 MPa, alternatively between about 1 and 2 MPa, alternatively between about 2 and 3 MPa, alternatively between about 3 and 4 MPa, alternatively between about 4 and 5 MPa. The liquid hourly space velocity can be between about 1 and 5 per hour, alternatively between about 1 and 3 per hour, alternatively between about 3 and 5 per hour, alternatively between about 1 and 2 per hour, alternatively between about 2 and 3 per hour, alternatively between about 3 and 4 per hour, alternatively between about 4 and 5 per hour.

The heavy aromatics feed stream to the conversion process can be a heavy reformate, generally including alkylaromatic hydrocarbons in the carbon number range C9 to C11+ that may include, for example, such hydrocarbons as propylbenzenes, ethylmethylbenzenes, tetramethylbenzenes, ethyldimethylbenzenes, diethylbenzenes, methylpropylbenzenes, and mixtures thereof.

The heavy aromatics feed stream, characterized mainly by C9+ aromatics, results in effective transalkylation of light aromatics such as benzene and toluene with the heavier C9+ aromatics, yielding additional C8 aromatics that are preferably xylenes. The heavy aromatics stream preferably comprises at least about 95% by weight C9 aromatics. In certain embodiments, the heavy aromatic feed steam can be derived from the same or different known refinery and petrochemical processes. In certain embodiments, the heavy aromatics feed stream can include, at least in part, feedstream that is recycled from the separation of the product stream and light gases from transalkylation.

Transalkylation of the feed stream can occur in the vapor phase and in the presence of hydrogen. The hydrogen is typically supplied with the feed stream, and with any optionally recycled hydrocarbons, in an amount from about 0.1 moles hydrogen per mole of alkylaromatics up to ten moles per mole of alkylaromatics (i.e., a hydrogen:alkylaromatic ratio of between about 0.1:1 and 10:1). In certain embodiments, the hydrogen:alkylaromatic ratio can be between about 0.1:1 and 2:1; alternatively between about 2:1 and 5:1, alternatively between about 5:1 and 10:1. This ratio of hydrogen to alkylaromatics may also referred to as the hydrogen-to-hydrocarbon ratio.

In certain embodiments, the heavy aromatic feed to the transalkylation reaction zone can be heated. For example, in certain embodiments, the feedstock can be heated first by indirect heat exchange against the effluent of the reaction zone, and then is heated to reaction temperature. The feedstock can then be passed through a reaction zone, which may include one or more individual reactors. In certain embodiments, the reactor includes a single reaction vessel having a fixed cylindrical bed of catalyst. In alternate embodiments, a moving catalyst bed or radial flow reactor, or combination of one or more of the above reactors, can be employed. Passage of the combined hydrogen and heavy aromatic feed through the reaction zone results in the production of an effluent stream comprising unconverted feed and the desired product hydrocarbons.

The transalkylation reaction uses the transalkylation catalyst described herein in at least one zone. The process can also include the use of additional catalysts. The heavier aromatic compounds present in the feedstock readily undergo conversion into lighter aromatics. The conditions employed in the transalkylation zone normally include a temperature of from about 200° C. to about 540° C., and moderately elevated pressures, broadly ranging from about 1 MPa to about 5 MPa.

The transalkylation catalyst utilized herein is based upon solid-acid materials combined with a metal component. Generally, the catalyst can include two solid-acid zeolite materials. The first solid-acid zeolite can include all forms and types of mordenite, beta zeolite, ZSM-5, ZSM-11, ZSM-12, ZSM-22, ZSM-23, MFI topology zeolite, NES topology zeolite, EU-1, MAPO-36, SAPO-5, SAPO-11, SAPO-34, and SAPO-41, and silica-alumina or ion-exchanged versions of such solid acids. The first zeolite can be present in an amount ranging from about 10 to 90% by weight of the total catalyst amount, in its final dried and calcined form.

The second zeolite incorporated in the catalyst recipe is different from the first zeolite in both physical and chemical characteristics, generally having a higher acidity, and is a zeolite that is also selected from the group including mordenite, beta zeolite, ZSM-5, ZSM-11, ZSM-12, ZSM-22, ZSM-23, MFI topology zeolite, NES topology zeolite, EU-1, MAPO-36, SAPO-5, SAPO-11, SAPO-34, and SAPO-41. The second zeolite can be present in an amount ranging from about 10 to 90% by weight of the total catalyst amount, in its final dried and calcined form.

The catalyst can optionally include a refractory binder or matrix to facilitate fabrication of the catalyst, provide strength to the catalyst, and reduce fabrication costs. The binder should be uniform in composition and relatively refractory to the conditions used in the process. Suitable binders can include inorganic oxides, such as one or more of alumina, magnesia, zirconia, chromia, titania, boria, phosphate, zinc oxide and silica. In certain embodiments, alumina can be used as the binder. Typically, the two zeolite materials are mixed with the alumina binder in dry powdered form to yield a homogeneous mixture, thus ensuring that a homogeneous composition of the extrudates formed therefrom.

The multimetal zeolites based catalyst also includes at least three metal components, selected from the Group 4 lanthanides, and the Group 6 and 10 metals. In certain embodiments, two of the preferred metal components are selected from Group 10, such as nickel and platinum metals, although palladium may be used in lieu of, or in addition to, platinum. In certain embodiments, a Group 6 metal, such as molybdenum, chromium or tungsten, can be included in the catalyst. The third metal component can be selected from the Group 4 lanthanides, such as cerium. In certain embodiments, the metal components can be included within the final catalytic composite as an oxide, sulfide, or halide, in chemical combination with one or more of the other ingredients of the composite. In certain embodiments, the Group 4 lanthanides can be included in elemental form. The metal component can be present in the final catalyst composite in an amount that is catalytically effective, for example between about 0.01% and 5% by weight of the final catalyst, calculated on an elemental basis. The metal component can be incorporated into the catalyst in by any suitable manner, such as co-precipitation or co-gelation with the carrier material, ion exchange, or impregnation.

EXAMPLES

In the examples provided herein, the exemplary heavy reformate used for testing in these examples had a composition as provided in Table 6.

TABLE 6

Composition of a typical heavy reformate.

| Major Hydrocarbons | Amount (wt %) |
| --- | --- |
| Isopropyl benzene | 1.8 |
| n-Propyl-benzene | 4.4 |
| 1-Methyl, 3-ethyl benzene | 18.5 |
| 1-Methyl, 4-ethyl benzene | 9.1 |
| 1,3,5-tri-methyl benzene | 10.1 |
| 1-Methyl,2-ethyl benzene | 6.5 |
| 1,2,4-trimethyl benzene | 39.1 |
| 1,2,3-trimethyl benzene | 6.6 |
| Total C9 Components | 96.1 |
| Total C10 Components | 3.9 |
| Total Components | 100 |

For exemplary purposes, a zeolite-mixed-zeolite multimetal catalyst according to the present invention, designated as Catalyst of the Example 1, was prepared and tested. The catalyst of the Example 1 has a zeolite-mixed-zeolite support, and includes three metal components loaded on the zeolite and alumina binder in a predefined fashion, and then mixed and bind together into extrudates.

Example 1

Preparation of the Catalyst of the Example 1

Beta zeolite (ammonium form, HSZ-940NHA, obtained from Tosoh Chemical Corporation, Japan), having an $SiO_2$/$Al_2O_3$ molar ratio of 37. BET surface area of 570 m2/g, a mean particle size 6 micron, and a nominal content of $Na_2O$ 0.05% by weight was used in the catalyst preparation. The Beta zeolite was stirred with nickel nitrate hexahydrate aqueous solution to ion-exchange nickel, and the solid that was obtained was dried and impregnated with platinum chloride aqueous solution to produce Ni-Beta-Pt according to the following procedure: Nickel nitrate hexahydrate, $Ni(NO_3)_2 \cdot 6H_2O$, was dissolved in distilled water to produce 200 mL of 10% by weight solution. 30 g of uncalcined Beta zeolite was added to this solution and stirred continuously for 1 hour, then filtered, and finally washed two times to remove the nitrate ions. The resulting solid was dried at room temperature for 2 hours, and then oven dried at 120° C. for 3 hours. The Ni-Beta was then impregnated with 0.1% by weight platinum solution. In this method based on the wettability test, 0.038 g of platinum chloride, $Pt(Cl)_2$, was dissolved in 36.1 g of distilled water. To dissolve the platinum chloride completely, 2.5 mL of ammonium hydroxide solution was added to the mixture with stirring. The Ni-Beta was then impregnated by incipient wetness method using this solution. The resultant solid was dried at room temperature for 2 hours and then oven dried at 120° C. for 3 hours. Then 4 g of alumina binder (Cataloid AP-3, obtained from CCIC, Japan) in dry powder form was dispersed in a 16 mL aqueous solution containing 0.62 g cerium nitrate. $Ce(NO_3)_3.6H_2O$, and stirred continuously for 30 minutes to prepare a homogenously dispersed alumina. To this mixture, 4 g of uncalcined and untreated ZSM-5 (CT-435, obtained from CATAL, UK) having silica to alumina molar ratio of 27 was added in powder form to the slurry. Subsequently 12 g of Ni-Beta-Pt was added and mixed thoroughly to produce a thick paste which was then converted into 1.0 mm extrudates. The ratio of Beta to ZSM-5 to AP3 was 3:1:1. The extrudates were dried at room temperature overnight, then dried in air-circulated oven at 120° C., and then calcined in a furnace at 500° C. for 3 hours. The catalyst developed can be symbolized as follows: [(Ni-Beta-Pt)+ZSM5+(Ce-AP3)].

Example 2

Testing of Catalyst of Example 1

The catalyst of Example 1 was tested for transalkylation reaction in a bench top reaction system using heavy reformate to test the effectiveness of the catalyst for C9 conversion and products selectivity. The testing method consisted of loading a vertical reactor with 2.0 ml of the catalyst extrudates in the middle of the reactor together with the inert alumina balls in the lower and upper parts of the reactor. The total volume of the reactor was 5 ml. The catalyst was activated and reduced under a flow of pure hydrogen at 50 mL/min gas and was maintained at a temperature of 400° C. for 2 hours. Then, the reactor temperature was reduced to 340° C. and 20 bars pressure and the heavy reformate was supplied at a rate of 4.8 mL/h. The composition of heavy reformate is provided in Table 6. The reaction was run for 3 hours at this temperature before collecting the sample. The reaction product was then directly injected into an on-line gas chromatograph equipped with a flame ionization detector. The hydrocarbon separation was carried out on a 50 meter long and 0.15 mm diameter column under temperature programmed conditions. The temperature was increased to 360° C. and the reaction was continued for 2 hours before analyzing the gas and liquid products. The reaction was also run at reaction temperatures of 380° C. and 400° C. In this manner, the reaction products were analyzed at 340° C., 360° C., 380° C. and 400° C. The components were separated according to their boiling points. The components were identified using a calibration based on a standard hydrocarbon mixture sample having the components of known composition. The composition of the gaseous product was analyzed off-line by a Shimadzu Model 14B gas chromatograph equipped with a flame ionization detector and thermal conductivity detector. The gaseous hydrocarbons and hydrogen were separated on an alumina PLOT, 50 meter capillary column. Various feed conversion levels were obtained at different temperatures and the results show low and high severity conversion of C9 components.

Tables 7 and 8 demonstrate that the Catalyst of the Example 1 shows relatively high C2-C4 petrochemical feedstock production at low severity reaction temperatures of 340° C. and 360° C., as well as at high severity reaction temperatures of 380° C. and 400° C.

The C6-C8 compositional data shown in Tables 9 and 10 demonstrates that the Catalyst of the Example 1 shows high production amount of mixed xylenes, at low severity reaction temperatures of 340° C. and 360° C., as well as at high severity reaction temperatures of 380° C. and 400° C. The data shows that the catalyst is quite active and gave high xylenes yields at low temperatures. The data also shows low benzene and toluene production, indicating low selectivity for C6 and C7 components. Ethylbenzene production was negligible at both low and high severity reaction conditions.

Tables 11 and 12 provide the C9-C10 product composition data at low reaction temperature of 340° C. and 360° C. as well as at high reaction temperature of 380° C. and 40° C.

Tables 13 and 14 show relatively high conversion of individual C9 hydrocarbons at low severity reaction temperatures of 340° C. and 360° C., as well as at high severity reaction temperature of 380° C. and 400° C. The data also shows that C9 hydrocarbons conversion was quite high even at low severity. Conversion of methyl-ethyl benzenes (MEBs) was higher as compared to trimethyl benzene (TMBs) conversion, thus showing xylenes production selectivity.

TABLE 7

C2-C4 Composition (vol %) of the reaction products obtained using the catalyst of the Example 1 at low severity reaction temperatures of 340° C. and 360° C., LHSV of 2.4 $h^{-1}$, and 20 bar hydrogen pressure.

| Temperature | Catalyst of Example 1 340° C. | Catalyst of Example 1 360° C. |
|---|---|---|
| C2 | 4.88 | 6.41 |
| C3 | 4.63 | 6.08 |
| C4 | 3.02 | 3.96 |

TABLE 8

C2-C4 Composition (vol %) of the reaction products obtained using the catalyst of the Example 1 at high severity reaction temperature of 380° C. and 400° C., hydrogen pressure of 20 bar, and LHSV of 2.4 $h^{-1}$.

| Temperature | Catalyst of Example 1 380° C. | Catalyst of Example 1 400° C. |
|---|---|---|
| C2 | 7.98 | 11.52 |
| C3 | 3.25 | 4.03 |
| C4 | 1.22 | 0.45 |

TABLE 9

C6-C8 Composition (wt %) of the reaction products obtained using the catalyst of the Example 1 at low severity reaction temperature of 340° C. and 360° C., hydrogen pressure of 20 bar, and LHSV of 2.4 $h^{-1}$.

| Temperature | Catalyst of Example 1 340° C. | Catalyst of Example 1 360° C. |
|---|---|---|
| LHSV | 2.4 | 2.4 |
| Benzene | 0.87 | 1.19 |
| Toluene | 10.49 | 13.10 |
| Ethylbenzene | 0.75 | 0.31 |
| p-xylene | 6.69 | 7.38 |
| m-xylene | 14.88 | 16.44 |
| o-xylene | 5.96 | 6.63 |
| Total Xylenes | 27.53 | 30.45 |

TABLE 10

C6-C8 Composition (wt %) of the reaction products obtained using the catalyst of the Example 1 at high severity reaction temperature of 380° C. and 400° C., hydrogen pressure of 20 bar, and LHSV of 2.4 h$^{-1}$.

| Temperature | Catalyst of Example 1 380° C. | Catalyst of Example 1 400° C. |
|---|---|---|
| Benzene | 1.86 | 1.32 |
| Toluene | 15.26 | 13.57 |
| Ethylbenzene | 0.17 | 0.00 |
| p-xylene | 7.65 | 7.74 |
| m-xylene | 16.90 | 17.06 |
| o-xylene | 6.94 | 7.17 |
| Total Xylenes | 31.49 | 31.97 |

TABLE 11

C9-C10 Composition (wt %) of the reaction products obtained using the catalyst of the Example 1 at low severity reaction temperature of 340° C. and 360° C., hydrogen pressure of 20 bar, and LHSV of 2.4 h$^{-1}$.

| Temperature | Catalyst of Example 1 340° C. | Catalyst of Example 1 360° C. |
|---|---|---|
| 1-methyl-4-ethyl benzene | 0.60 | 0.43 |
| 1-methyl-3-ethyl benzene | 1.77 | 1.18 |
| 1,3,5-trimethyl benzene | 6.08 | 6.44 |
| 1-methyl-2-ethyl benzene | 0.43 | 0.34 |
| 1,2,4-trimethyl benzene | 13.49 | 15.02 |
| 1,4-diethyl benzene | 1.03 | 0.58 |
| 1,2,3-trimethyl benzene | 1.66 | 2.01 |
| 1,2-diethyl benzene | 0.83 | 0.39 |
| 1,2,4,5-tetramethyl benzene | 1.91 | 1.52 |
| 1,2,3,5-tetramethyl benzene | 2.42 | 1.93 |
| 1,2,3,4-tetramethyl benzene | 0.54 | 0.54 |

TABLE 12

C9-C10 Composition (wt %) of the reaction products obtained using the catalyst of the Example 1 at high severity reaction temperature of 380° C. and 400° C., hydrogen pressure of 20 bar, and LHSV of 2.4 h$^{-1}$.

| Temperature | Catalyst of Example 1 380° C. | Catalyst of Example 1 400° C. |
|---|---|---|
| 1-methyl-4-ethyl benzene | 0.00 | 0.00 |
| 1-methyl-3-ethyl benzene | 0.36 | 0.20 |
| 1,3,5-trimethyl benzene | 6.20 | 6.15 |
| 1-methyl-2-ethyl benzene | 0.00 | 0.00 |
| 1,2,4-trimethyl benzene | 14.02 | 14.12 |
| 1,4-diethyl benzene | 0.22 | 0.00 |
| 1,2,3-trimethyl benzene | 1.81 | 1.87 |
| 1,2-diethyl benzene | 0.18 | 0.00 |
| 1,2,4,5-tetramethyl benzene | 1.41 | 1.42 |
| 1,2,3,5-tetramethyl benzene | 1.77 | 1.77 |
| 1,2,3,4-tetramethyl benzene | 0.42 | 0.42 |

TABLE 13

Conversion (wt %) of C9 hydrocarbons at low severity reaction temperature of 340° C. and 360° C., at LHSV of 2.4 h$^{-1}$, using the Catalyst of Example 1.

| Temperature | Catalyst of Example 1 340° C. | Catalyst of Example 1 360° C. |
|---|---|---|
| LHSV | 2.4 | 2.4 |
| 123TMB Conversion | 74.85 | 69.55 |
| 124TMB Conversion | 65.50 | 62.07 |
| 135TMB Conversion | 39.80 | 36.24 |
| Total TMBs Conversion | 61.95 | 57.94 |
| 1M2EB Conversion | 93.38 | 94.77 |
| 1M3EB Conversion | 90.43 | 93.62 |
| 1M4EB Conversion | 93.41 | 95.27 |
| Total MEBs Conversion | 91.79 | 94.28 |

TABLE 14

Conversion (wt %) of individual C9 hydrocarbons at high severity reaction temperature of 380° C. and 400° C. LHSV of 2.4 h$^{-1}$, using the Catalyst of Example 1.

| Temperature | Catalyst of Example 1 380° C. | Catalyst of Example 1 400° C. |
|---|---|---|
| 123TMB Conversion | 72.58 | 71.67 |
| 124TMB Conversion | 64.60 | 64.34 |
| 135TMB Conversion | 38.61 | 39.11 |
| Total TMBs Conversion | 60.52 | 60.32 |
| 1M2EB Conversion | 100.00 | 100.00 |
| 1M3EB Conversion | 98.05 | 98.92 |
| 1M4EB Conversion | 100.00 | 100.00 |
| Total MEBs Conversion | 98.94 | 99.41 |

Although the present invention has been described in detail, it should be understood that various changes, substitutions, and alterations can be made hereupon without departing from the principle and scope of the invention. Accordingly, the scope of the present invention should be determined by the following claims and their appropriate legal equivalents.

The singular forms "a", "an" and "the" include plural referents, unless the context clearly dictates otherwise.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

Throughout this application, where patents or publications are referenced, the disclosures of these references in their entireties are intended to be incorporated by reference into this application, in order to more fully describe the state of the art to which the invention pertains, except when these references contradict the statements made herein.

As used herein and in the appended claims, the words "comprise," "has," and "include" and all grammatical variations thereof are each intended to have an open, non-limiting meaning that does not exclude additional elements or steps.

As used herein, terms such as "first" and "second" are arbitrarily assigned and are merely intended to differentiate between two or more components of an apparatus. It is to be understood that the words "first" and "second" serve no other purpose and are not part of the name or description of the component, nor do they necessarily define a relative location or position of the component. Furthermore, it is to be under- That which is claimed is:

1. A transalkylation catalyst for the conversion of a heavy reformate feedstock into a xylenes-rich product stream and a C2 through C4 hydrocarbon product stream, the transalkylation catalyst consisting of:
- a beta zeolite in ammonium form, containing $Na_2O$ present in an amount of 0.05% by weight, based on the total weight of the beta zeolite in ammonium form;
- ZSM-5;
- nickel;
- platinum;
- cerium; and
- alumina;
- wherein the beta zeolite in ammonium form, ZSM 5 and alumina are present in a ratio of 3:1:1.

2. The catalyst of claim 1 wherein the pore size of the beta zeolite in ammonium form and the ZSM 5 are different.

3. The catalyst of claim 1 wherein the beta zeolite in ammonium form is present in an amount of between about 10% and 90% by weight of the total transalkylation catalyst weight.

4. The catalyst of claim 1, wherein the ZSM-5 is present in an amount of between about 10% and 90% by weight of the total transalkylation catalyst weight.

5. The catalyst of claim 1, wherein the nickel, platinum and cerium components are each present in an amount of between about 0.01% and 5% by weight of the total transalkylation catalyst weight.

6. The catalyst of claim 1, wherein the catalyst operates in a transalkylation reaction zone at a temperature of between about 200° C. and 540° C.

7. The catalyst of claim 1, wherein the catalyst operates in a transalkylation reaction zone at a pressure of between about 1 MPa and 5 MPa.

8. The catalyst of claim 1, wherein the catalyst operates in a transalkylation reaction zone wherein the ratio of hydrogen to heavy reformate is between about 0.1:1 and 10:1.

* * * * *